(12) United States Patent
Zou et al.

(10) Patent No.: US 10,046,109 B2
(45) Date of Patent: Aug. 14, 2018

(54) DRUG DELIVERY DEVICE WITH COMPRESSIBLE DRUG RESERVOIR

(75) Inventors: Hans Zou, Windsor, NJ (US); Jeff Shimizu, Cortlandt Manor, NY (US); Johan Frederik Dijksman, Weert (NL)

(73) Assignee: Progenity, Inc., San Diego, CA (US)

(*) Notice: Subject to any disclaimer, the term of this patent is extended or adjusted under 35 U.S.C. 154(b) by 841 days.

(21) Appl. No.: 13/390,111

(22) PCT Filed: Aug. 10, 2010

(86) PCT No.: PCT/IB2010/053610
§ 371 (c)(1),
(2), (4) Date: Feb. 7, 2013

(87) PCT Pub. No.: WO2011/018753
PCT Pub. Date: Feb. 17, 2011

(65) Prior Publication Data
US 2013/0204233 A1 Aug. 8, 2013

Related U.S. Application Data

(60) Provisional application No. 61/233,187, filed on Aug. 12, 2009.

(51) Int. Cl.
*A61M 5/145* (2006.01)
*A61M 31/00* (2006.01)

(52) U.S. Cl.
CPC ........ *A61M 5/1452* (2013.01); *A61M 31/002* (2013.01)

(58) Field of Classification Search
CPC ........ A61M 5/20; A61M 5/145; A61M 5/315; A61M 5/31513; A61M 2005/3151
(Continued)

(56) References Cited

U.S. PATENT DOCUMENTS 4,102,998 A 7/1978 Gutnick
4,236,516 A * 12/1980 Nilson .................... A61J 1/062
222/107

(Continued)

FOREIGN PATENT DOCUMENTS

CN 1958090 5/2007
DE 3339323 5/1985
(Continued)

OTHER PUBLICATIONS

The Chinese Office Action dated Sep. 6, 2013 for Chinese patent application No. 201080040663.6, a counterpart foreign application of U.S. Appl. No. 13/390,111, 4 pages.
(Continued)

*Primary Examiner* — Laura Bouchelle
(74) *Attorney, Agent, or Firm* — Roger D. Emerson; Emerson, Thomson & Bennett, LLC

(57) ABSTRACT

A drug delivery device (50) is provided comprising a drug reservoir (10) and a piston (11). The drug reservoir (10) is provided for comprising a drug and comprises a flexible wall (22) and a dispensing hole (15) for dispensing the drug into an environment of the drug de delivery device (50). The piston (11) is provide for pressing against the flexible wall (22) to compress the drug reservoir (10) for pushing an amount of the drug through the dispensing hole (15). An adhesion interface (51) between a surface of the piston (11) and the flexible wall (22) prevents sliding between the surface of the piston (11) and the flexible wall (22).

17 Claims, 4 Drawing Sheets

(58) Field of Classification Search
USPC ..... 604/891.1, 131, 132, 142, 151, 153, 154
See application file for complete search history.

(56) References Cited

U.S. PATENT DOCUMENTS

| | | | |
|---|---|---|---|
| 4,457,752 A * | 7/1984 | Vadasz | 604/135 |
| 4,564,363 A | 1/1986 | Bagnall et al. | |
| 4,572,403 A | 2/1986 | Benaroya | |
| 4,814,180 A | 3/1989 | Eckenhoff et al. | |
| 5,071,040 A | 12/1991 | Laptewicz, Jr. | |
| 5,170,801 A | 12/1992 | Casper et al. | |
| 5,279,607 A | 1/1994 | Schentag et al. | |
| 5,318,557 A | 6/1994 | Gross | |
| 5,423,779 A | 6/1995 | Yeh | |
| 5,567,592 A | 10/1996 | Benet et al. | |
| 5,728,396 A | 3/1998 | Peery et al. | |
| 5,853,386 A | 12/1998 | Davis et al. | |
| 6,053,899 A | 4/2000 | Slanda et al. | |
| 6,182,941 B1 | 2/2001 | Scheurenbrand et al. | |
| 6,423,779 B2 | 7/2002 | Sue et al. | |
| 6,485,471 B1 * | 11/2002 | Zivitz et al. | 604/212 |
| 6,632,216 B2 | 10/2003 | Houzego et al. | |
| 6,699,214 B2 | 3/2004 | Gellman | |
| 6,776,165 B2 | 8/2004 | Jin | |
| 6,800,060 B2 | 10/2004 | Marshall | |
| 6,803,373 B2 | 10/2004 | Schellens | |
| 6,929,636 B1 | 8/2005 | von Alten | |
| 7,014,640 B2 | 3/2006 | Kemppainen et al. | |
| 7,030,132 B2 | 4/2006 | Schellens et al. | |
| 8,021,357 B2 | 9/2011 | Tanaka et al. | |
| 8,100,889 B2 | 1/2012 | Kawano et al. | |
| 8,308,681 B2 | 11/2012 | Slocum et al. | |
| 2002/0072735 A1 | 6/2002 | Kupperblatt et al. | |
| 2003/0020810 A1 | 1/2003 | Takizawa et al. | |
| 2003/0213495 A1 | 11/2003 | Fujita et al. | |
| 2004/0242962 A1 | 12/2004 | Uchiyama | |
| 2004/0267240 A1 | 12/2004 | Gross et al. | |
| 2004/0267241 A1 | 12/2004 | Russell | |
| 2005/0147559 A1 | 7/2005 | von Alten | |
| 2005/0222537 A1 | 10/2005 | Dinsmoor et al. | |
| 2006/0145876 A1 | 7/2006 | Kimura et al. | |
| 2006/0155174 A1 | 7/2006 | Glukhovsky et al. | |
| 2007/0138027 A1 | 6/2007 | Dinsmoor et al. | |
| 2007/0213659 A1 | 9/2007 | Trovato et al. | |
| 2010/0280464 A1 | 11/2010 | De Graaff et al. | |

FOREIGN PATENT DOCUMENTS

| | | |
|---|---|---|
| FR | 2794654 | 12/2000 |
| JP | 2001526939 | 12/2001 |
| JP | 2002532162 | 10/2002 |
| JP | 2003520108 | 7/2003 |
| JP | 2005511184 | 4/2005 |
| JP | 2005536307 | 12/2005 |
| WO | WO03008637 | 1/2003 |
| WO | WO03068061 | 8/2003 |
| WO | WO2005025647 | 3/2005 |
| WO | WO2005038049 | 4/2005 |
| WO | WO2006021932 | 3/2006 |
| WO | WO2006025013 | 3/2006 |
| WO | WO2006044049 | 4/2006 |
| WO | WO2006056944 | 6/2006 |
| WO | WO2006077527 | 7/2006 |
| WO | WO2006077529 | 7/2006 |
| WO | WO2008029372 | 3/2008 |
| WO | WO2008038199 | 4/2008 |
| WO | WO2008062335 | 5/2008 |
| WO | WO 2008062335 A1 * | 5/2008 |
| WO | WO2010086681 | 8/2010 |

OTHER PUBLICATIONS

The Chinese Office Action dated Jan. 15, 2013 for Chinese patent application No. 201080015953.5, a counterpart foreign application of U.S. Appl. No. 13/262,841, 17 pages.

The Chinese Office Action dated Jan. 21, 2013 for Chinese patent application No. 201080040663.6, a counterpart foreign application of U.S. Appl. No. 13/390,111, 8 pages.

The Chinese Office Action dated Mar. 14, 2013 for Chinese patent application No. 200980112018.8, a counterpart foreign application of U.S. Appl. No. 12/933,891, 12 pages.

The Chinese Office Action dated May 13, 2013 for Chinese patent application No. 201080015284.1, a counterpart foreign application of U.S. Appl. No. 13/262,861, 11 pages.

The Chinese Office Action dated Aug. 5, 2013 for Chinese patent application No. 201080015953.5, a counterpart foreign application of U.S. Appl. No. 13/262,841, 7 pages.

The European Office Action dated Jul. 25, 2013 for European patent application No. 10779040.4, a counterpart foreign application of U.S. Appl. No. 13/498,835, 4 pages.

Evans, et al., "Measurement of Gastrointestinal pH Profiles in Normal Ambulant Human Subjects", GUT, vol. 29, 1988, pp. 1035-1041.

Hindmarsh et al., "Height Monitoring as a diagnostic test", at www.archdischild.com, Arch Dis Child, 2004, 2 pages.

The Japanese Office Action dated Apr. 16, 2013 for Japanese Patent Applicaiton No. 2011-514179, a counterpart foreign application of U.S. Appl. No. 12/992,305, 9 pages.

The Japanese Office Action dated Apr. 23, 2013 for Japanese patent application No. 2012-524322, a counterpart foreign application of U.S. Appl. No. 13/390,111, 6 pages.

The Japanese Office Action dated Apr. 30, 2013 for Japanese patent application No. 2010-546431, a counterpart foreign application of U.S. Appl. No. 12/867,888, 4 pages.

The Japanese Office Action dated Jun. 25, 2013 for Japanese patent application No. 2012531527, a counterpart foreign application of U.S. Appl. No. 13/498,835, 8 pages.

Kompella, et al., "Delivery System for Penetration Enhancement of Peptide and Protein Drugs: Design Considerations", Advanced Drug Delivery Reviews, vol. 46, 2001, pp. 211-245.

Office action for U.S. Appl. No. 12/992,305, dated Jul. 16, 2013, Zou et al., "Device for Delivery of Powder Like Medication in a Humid Environment", 14 pages.

Non-Final Office Action for U.S. Appl. No. 11/720,242, dated Jul. 3, 2013, Gerardus Rudolph Langereis et al., "Electronically Controlled Pill and System Having at Least One Sensor for Delivering at Least One Medicament", 22 pages.

Office action for U.S. Appl. No. 13/262,861, dated Aug. 2, 2013, Shimizu et al., "Valveless Drug Delivery Device", 8 pages.

Office action for U.S. Appl. No. 12/867,888, dated Sep. 11, 2013, Shimizu, "Administration of Drugs to a Patient", 11 pages.

Paine, et al., "Characterization of Interintestinal and Intraintestinal Variations in Human CYP3A-Dependent Metabolism", The Journal of Pharmacology and Experimental Therapeutics, vol. 283, No. 3, 1997, pp. 1552-1562.

Siccardi, et al., "Regulation of Intestinal Epithelial Function: A Link Between Opportunities for Macromolecular Drug Delivery and Inflammatory Bowel Disease", Advanced Drug Delivery Reviews, vol. 57, 2005, pp. 219-235.

* cited by examiner

DRUG DELIVERY DEVICE WITH COMPRESSIBLE DRUG RESERVOIR

FIELD OF THE INVENTION

This invention relates to a drug delivery device, comprising a piston and a drug reservoir for comprising a drug and a piston. The drug reservoir comprises a flexible wall, and a dispensing hole for dispensing the drug into an environment of the drug delivery device. The piston is arranged for pressing against the flexible wall to compress the drug reservoir for pushing an amount of the drug through the dispensing hole.

BACKGROUND OF THE INVENTION

Such a drug delivery device may comprise a small sized electrical motor, e.g. stepper motor, of which the action is controlled by an on-board microprocessor. The stepper motor moves the piston forward against the wall, e.g. pushed by a screw rod mechanism. The piston is moved in a controlled way as far as speed and stroke are considered. The piston pushes the flexible wall into the drug reservoir. As a result, the volume of the drug reservoir decreases and the pressure inside the drug reservoir increases. The increasing pressure causes an amount of the drug to be pushed out of the dispensing hole. While the piston pushes the flexible wall into the drug reservoir, it takes a shape that corresponds to minimum surface energy. Such shapes usually are irregular, resulting in a smaller usable drug reservoir volume and a higher resistance for the piston to move forward. When the drug reservoir becomes emptier, the flexible wall starts to fold until the piston can no longer overcome resistance from the folds and the drug viscosity and stops dispensing. When the piston stops dispensing, drugs stay behind in the folds. Consequently, it is not possible to fully empty the drug reservoir. Additionally, there is a problem of the piston sliding along the folded flexible wall surface without causing any drug to be pushed out of the dispensing hole because the piston mechanism cannot be effective.

OBJECT OF THE INVENTION

It is an object of the invention to provide a drug delivery device as described above, wherein the drug reservoir can be emptied more reliably.

SUMMARY OF THE INVENTION

According to a first aspect of the invention, this object is achieved by providing a drug delivery device, comprising a drug reservoir, a piston and an adhesion interface. The drug reservoir comprises a flexible wall and a dispensing hole for dispensing the drug into an environment of the drug delivery device. The piston is arranged for pressing against the flexible wall to compress the drug reservoir for pushing an amount of the drug through the dispensing hole. The adhesion interface is situated between a surface of the piston and the flexible wall for preventing sliding between the surface of the piston and the flexible wall.

The adhesion interface keeps the flexible wall surface conformed to the piston surface and prevents both surfaces from slipping between each other. With every step of the piston into the flexible wall and in the direction of the delivery hole, a greater part of its surface gets covered by and adheres to the flexible wall surface. The flexible wall surface does not fold, but is slid around the piston surface.

The adhesion interface may, e.g., be a sticky coating on the piston surface and/or on the flexible wall. Alternatively, a magnetic coating is used on at least one of the two surfaces for providing the required adhesion.

In a preferred embodiment, the flexible wall comprises at least one non-flexible part located at the adhesion interface. An advantage of a non-flexible part is that it cannot be folded or wrinkled. When the piston pushes against a non-flexible part, its shape does not change. The flexible parts of the flexible wall meanwhile ensure that the flexible wall as a whole is still deformable and can be used for compressing the drug reservoir.

In a flexible wall with only one or a few non-flexible parts, the surface of the non-flexible parts preferably follows the contours of the piston surface at the contact area of both surfaces. This ensures an optimal distribution of the pressure exerted by the piston upon the flexible wall and further facilitates the emptying of the reservoir. In addition, the preformed flexible wall makes it easier to fill the reservoir to the right dose without the piston already placed against the flexible wall.

These and other aspects of the invention are apparent from and will be elucidated with reference to the embodiments described hereinafter.

DETAILED DESCRIPTION OF THE INVENTION

Figure 1:
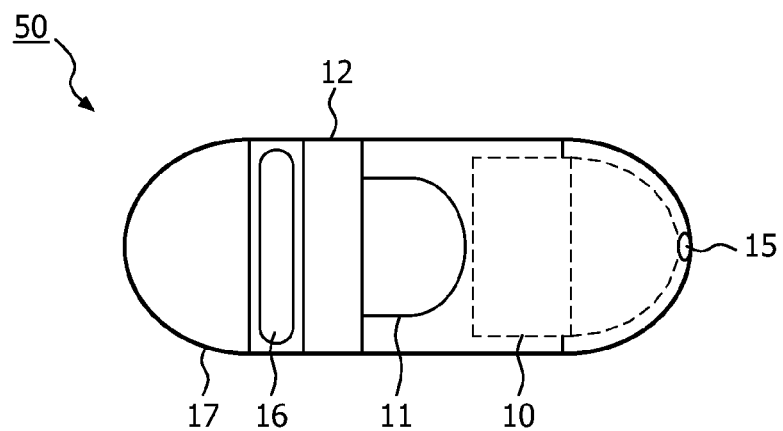
FIG. 1 shows a drug delivery device according to the invention.

FIG. 1 shows a drug delivery device 50 according to the invention. The drug delivery device 50 is a swallowable capsule comprising a drug to be released somewhere along the gastro-intestinal tract of a patient and an actuation mechanism 11, 12 for controlling the amount of drugs to be released and the moment of said release. It is to be noted that the current invention may also be used with implantable drug delivery devices. The drug to be released is stored in a compressible medicine reservoir 10. The drug may, e.g., be stored as dry powder, dissolved in water or as a gel or liquid.

The actuation mechanism 11, 12 comprises a piston 11 and a small sized electrical motor, e.g. a stepper motor 12, for pushing the piston by means of a screw rod mechanism towards the drug reservoir 10. Instead of a stepper motor 12, different driving means may be used for driving the piston 12. The driving of the piston 11 may, e.g., be realized using (electro-)magnetic forces or a swelling agent. When the piston 11 is pressed against the medicine reservoir 10, the medicine reservoir is compressed and the pressure inside the medicine reservoir 10 increases. As a result of the increasing pressure, the drug is pushed out of the drug delivery device 50 through a dispensing hole 15. The drug release may, e.g., be triggered by an internal clock, sensor values from a pH-sensor or trigger signals from an electrical or chemical detector element. If the drug delivery device 50 comprises means for wireless communication, the drug delivery may be externally triggered. The operations of all electronic functions of the device 50 are controlled by a microprocessor 17 and powered by a battery 16.

Figure 2:
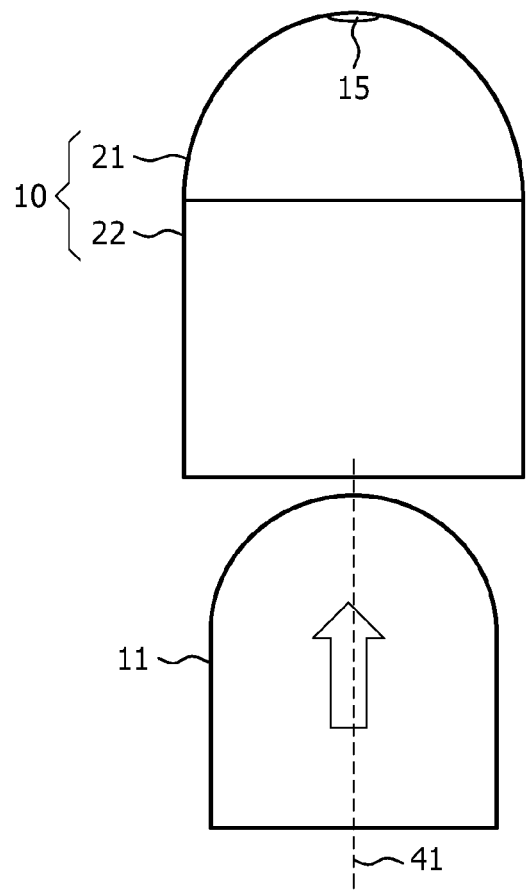
FIG. 2 shows a piston and an uncompressed drug reservoir.

FIG. 2 shows a piston 11 and an uncompressed drug reservoir 10. The drug reservoir 10 comprises a rigid dome shaped cap 21 and a flexible wall 22. The drug reservoir 10 shown in FIG. 2 is an example of a drug reservoir for which the current invention would be advantageous. The invention will however also improve the emptying of other drug reservoirs 10 with a flexible wall. For example, the complete drug reservoir 10 may be flexible or the dome shaped cap 21 and/or the flexible wall 22 may have different shapes than shown in the Figure. When the piston 11 is driven into the flexible wall 22 of the drug reservoir 10, the reservoir volume is compressed and an amount of the drug is released through the delivery hole 15.

Figure 3:
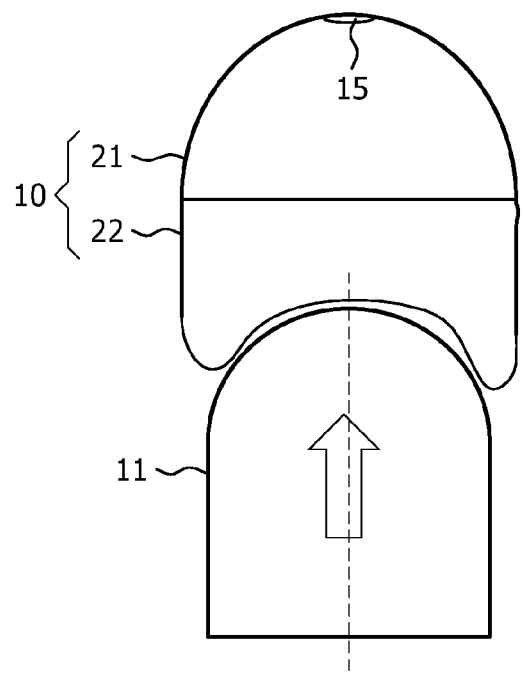
FIGS. 3 and 4 show partially compressed drug reservoirs in a drug delivery device according to the prior art.
Figure 4:
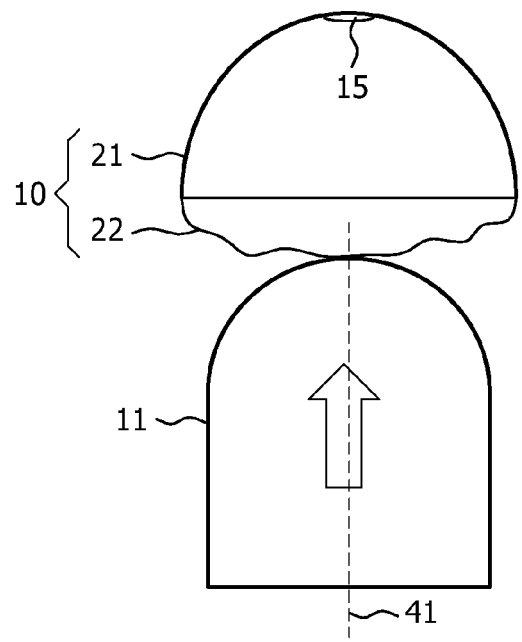

FIGS. 3 and 4 show partially compressed drug reservoirs 10 in a drug delivery device according to the prior art. In both Figures the flexible parts 22 of the drug reservoirs are compressed, while the dome shaped cap 21 keeps its shape. In FIG. 3, the flexible wall 22 has been compressed to a lesser extent than in FIG. 4. In FIG. 3 it is already visible that, due to uneven surface tension, the flexible wall shape does not conform to the piston 11 profile. This will result in an increased resistance for the piston 11 and drugs staying behind in folds of the flexible wall 22. As can be seen in FIG. 4, uneven surface tension and drug viscosity may cause the flexible wall 22 of a half full drug reservoir 10 to form multiple folds. Such folds increase the resistance to the piston 11 and may completely stop the dispensing of the drugs. In addition, the folds reduce the contact area between the flexible wall 22 and the piston 11, leading to slip between both and the piston not moving along its central axis 41 because the screw rod mechanism does not function properly.

Figure 5:
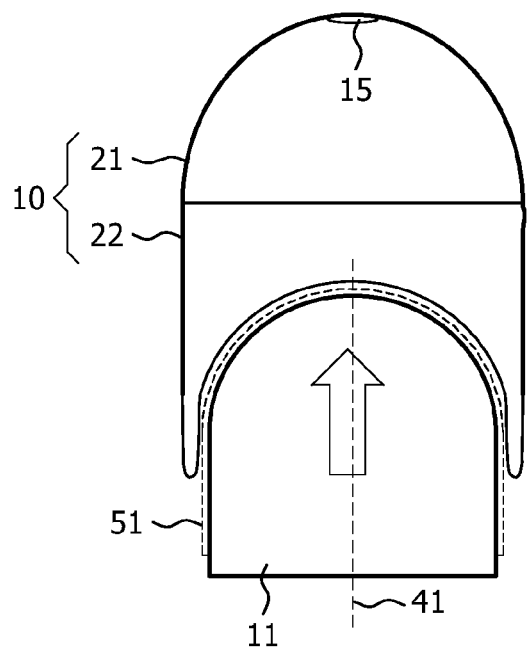
FIG. 5 shows a partly compressed drug reservoir in a drug delivery device according to the invention.

FIG. 5 shows a partly compressed drug reservoir 10 in a drug delivery device 50 according to the invention. In this embodiment, the problems of the prior art are solved by the introduction of an adhesion interface 51 in between the piston 11 and the flexible wall 22. The adhesion interface 51 keeps the flexible wall 22 conformed to the piston 11 surface and thus prevents slipping between both surfaces and folding of the flexible wall 22. The adhesion 51 may cover the complete piston 11 surface and/or the complete surface of the flexible wall 22. In a preferred embodiment the adhesion surface 51 only covers the parts of those surfaces which are designed to make contact with each other. Alternatively, the adhesion surface 51 may cover only part of the expected contact area.

The adhesion surface 51 may be a sticky surface applied to the piston 11 and/or flexible wall 22 surface. Alternatively, a magnetic coating may cover one of the surfaces, while the other surface is either magnetic or magnetizable. Another option is to use electrostatic interaction using an electrostatically charged polymer. A skilled person will be able to come up with many other possible ways of providing a suitable adhesion surface 51. The adhesion surface 51 used is preferably such that the drug reservoir 10 can still be removed from the adhered piston 11 surface for enabling refilling of the drug reservoir 10 without damaging the piston 11 or the drug reservoir. It is preferable that also the adhesion layer 51 keeps intact when the drug reservoir 10 and the piston 11 are separated. Alternatively, the drug reservoir 10 and/or the adhesion layer 51 are replaced when preparing the drug delivery device 50 for a second use.

Such an adhesion layer 51, which makes it possible to separate the surfaces without damaging the piston 11 or the reservoir 10, also enables a further option. When the reservoir 10 is completely or partly compressed and the piston 11 movement is reversed, the pressure inside the reservoir 10 will drop and body fluid will be sucked into the reservoir 10.

Figure 6:
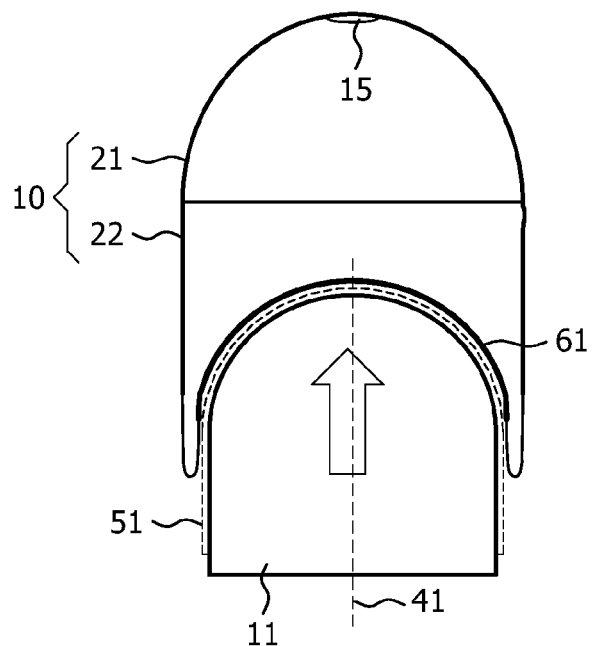
FIG. 6 shows a partly compressed drug reservoir with a non-flexible part in the flexible wall.

FIG. 6 shows a partly compressed drug reservoir 10 with a non-flexible part 61 in the flexible wall 22. The shape of the non-flexible part 61 follows the contours of the opposing piston 11 surface. In this embodiment this means that the non-flexible part 61 is dome shaped. An advantage of this non-flexible part 61 is that it cannot be folded or wrinkled. When the piston pushes against the non-flexible part 61, its shape does not change. The flexible parts of the flexible wall 22 meanwhile ensure that the flexible wall 22 as a whole is still deformable and that drug reservoir 10 is still compressible.

The non-flexible part 61 ensures an optimal distribution of the pressure exerted by the piston 11 upon the flexible wall 22 and further facilitates the emptying of the reservoir 10. In addition, the preformed flexible wall 22 makes it easier to fill the reservoir to the right dose without the piston 11 already placed against the flexible wall 22. If a fully flexible drug reservoir 10 would be filled to the rim, the viscosity of the drug may result in too much resistance for the piston to start moving.

Figure 7:
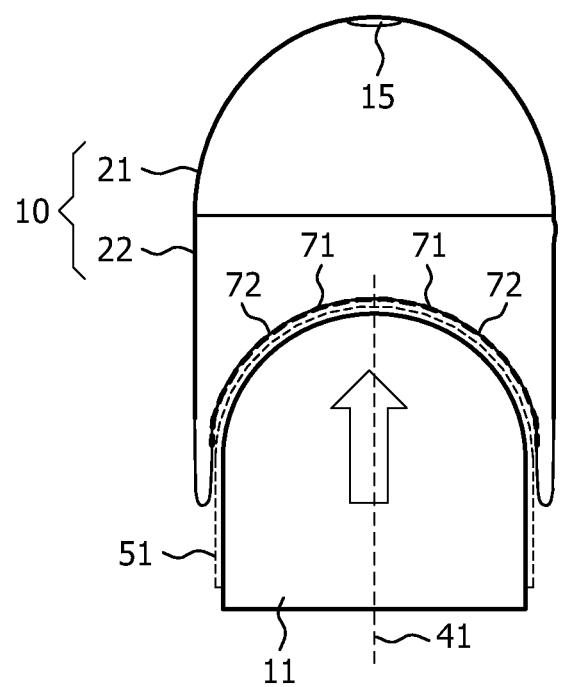
FIG. 7 shows a partly compressed drug reservoir with multiple rigid parts in the flexible wall.

FIG. 7 shows a partly compressed drug reservoir 10 with multiple rigid parts 71 in the flexible wall. The rigid parts 71 are alternated with flexible parts 72 for providing the required flexibility to the flexible wall 22.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A capsule, comprising:
   a reservoir defining a volume for containing a substance, the reservoir comprising a flexible wall and a hole providing a fluid passageway between the reservoir and an environment;
   a piston disposed on a side of the flexible wall opposite the volume, the piston comprising an outer surface proximate a side of the flexible wall opposite the volume;
   an adhesion interface adhering the outer surface of the piston to the side of the flexible wall opposite the volume to maintain conformity of the flexible wall to the piston, and
   wherein at least one of the following holds: (1) the adhesion surface comprises a sticky coating on the surface of the piston, the sticky coating comprising a silicon based resin, (2) the adhesion surface comprises a magnetic coating, or (3) the adhesion surface comprises an electrostatically charged polymer.

2. The capsule of claim 1, wherein the adhesion interface comprises a sticky coating on the surface of the piston and wherein the sticky coating comprises a silicon based resin.

3. The capsule of claim 1, wherein the adhesion interface comprises a sticky coating on the flexible wall.

4. The capsule of claim 1, wherein the adhesion surface comprises a magnetic coating.

5. The capsule of claim 1, wherein the adhesion surface comprises an electrostatically charged polymer.

6. The capsule of claim 1, wherein the flexible wall comprises at least one non-flexible part located at the adhesion interface.

7. The capsule of claim 1, wherein the drug delivery device is a swallowable drug delivery device.

8. The capsule of claim 1, wherein the drug delivery device is an implantable drug delivery device.

9. The capsule of claim 1, further comprising an actuator for moving the piston relative to the hole in at least one of a first direction to compress the reservoir or a second direction to expand the reservoir.

10. The capsule of claim 1, wherein the reservoir contains a substance to be dispensed, the piston being configured be pressed against the flexible wall to compress the reservoir and push an amount of the substance to be dispensed through the hole.

11. The capsule of claim 1, wherein the piston is configured to be moved away from the hole and the adhesion interface retains the flexible wall against the piston to expand the reservoir, the expansion causing contents from the environment to enter the reservoir via the hole.

12. A capsule comprising:
a housing comprising a rigid, dome-shaped cap;
an opening through the rigid, dome-shaped cap;
a reservoir in the housing defined at least in part by a flexible wall spaced from the opening and an internal surface of the rigid, dome-shaped cap;
a piston disposed in the housing on a first side of the flexible wall opposite the opening and arranged to contact the first side of the flexible wall, the flexible wall separating the piston from contents in the reservoir, the piston being movable relative to the opening, and a portion of the piston having a domed shape; and
an adhesion interface adhering a portion of the first side of the flexible wall to a portion of the piston, the adhesion interface maintaining conformity of the flexible wall to the portion of the piston having the domed shape.

13. The capsule of claim 12, wherein the flexible wall comprises at least one non-flexible p art and the non-flexible part is adhered to the piston at the adhesion surface.

14. The capsule of claim 12, wherein the adhesion surface comprises a sticky coating on the portion of the piston or on the surface of the flexible wall.

15. The capsule of claim 12, wherein the adhesion surface comprises a magnetic interface.

16. The capsule of claim 12, wherein the adhesion surface comprises an electrostatic charge.

17. The capsule of claim 12, wherein the reservoir is removable from the housing for refilling or replacement and the adhesion surface is remains intact on the piston when the reservoir is removed for refilling or replacement.

* * * * *